(12) United States Patent
Miyakoshi et al.

(10) Patent No.: US 10,298,002 B2
(45) Date of Patent: May 21, 2019

(54) AUXILIARY ARTIFICIAL HEART SYSTEM

(71) Applicant: SUN MEDICAL TECHNOLOGY RESEARCH CORPORATION, Suwa-shi, Nagano (JP)

(72) Inventors: Takayuki Miyakoshi, Shiga (JP); Seitarou Onuma, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 0 days.

(21) Appl. No.: 15/817,313

(22) Filed: Nov. 20, 2017

(65) Prior Publication Data
US 2018/0145494 A1 May 24, 2018

(30) Foreign Application Priority Data
Nov. 21, 2016 (JP) ................. 2016-226300

(51) Int. Cl.
*H02G 15/00* (2006.01)
*H02G 15/007* (2006.01)
*A61M 1/10* (2006.01)
*A61M 1/12* (2006.01)
*A61M 39/10* (2006.01)

(52) U.S. Cl.
CPC .......... *H02G 15/007* (2013.01); *A61M 1/102* (2014.02); *A61M 1/1008* (2014.02); *A61M 1/122* (2014.02); *A61M 1/127* (2013.01); *A61M 39/10* (2013.01)

(58) Field of Classification Search
CPC ...... A61M 1/008; A61M 1/102; A61M 1/122; H02G 15/007

USPC ......................................................... 174/151
See application file for complete search history.

(56) References Cited

U.S. PATENT DOCUMENTS

| 4,812,132 | A | * | 3/1989 | Gunnarsson | ........... H02G 11/02 439/13 |
| 7,148,431 | B2 | * | 12/2006 | Pyron | ................. H02G 3/0691 174/656 |
| 8,791,377 | B2 | * | 7/2014 | Jafari | ................... H02G 3/0691 174/660 |
| 9,111,428 | B2 | * | 8/2015 | Fawcett | ............. G08B 13/1463 |

(Continued)

FOREIGN PATENT DOCUMENTS

JP 2016-86600 A 5/2016

*Primary Examiner* — Dhiru R Patel
(74) *Attorney, Agent, or Firm* — Hauptman Ham, LLP

(57) ABSTRACT

A cable protector includes: a helical portion where a helical strip-like member surrounds a barrel portion of a cable, an equipment housing mounting portion configured to surround the barrel portion between a rear end portion of the strip-like member and an equipment housing, and a distal cylindrical portion configured to surround the barrel portion. The equipment housing mounting portion includes a mounting plate and a cylindrical body. The equipment housing mounting portion forms a notched portion thereon for allowing entering and exiting of the barrel portion into and from the mounting plate. The distal cylindrical portion has an opening/closing portion changeable between a surrounding state where the distal cylindrical portion surrounds the barrel portion and a state which allows entering and exiting of the barrel portion into and from the distal cylindrical portion.

5 Claims, 6 Drawing Sheets

(56) References Cited

U.S. PATENT DOCUMENTS 9,634,475 B2 * 4/2017 Mason .................. H02G 15/007
9,913,532 B1 * 3/2018 Jones ....................... A47B 9/02

* cited by examiner

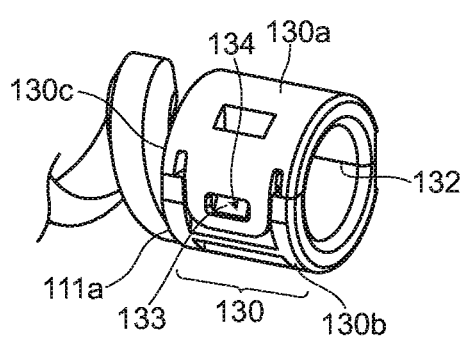
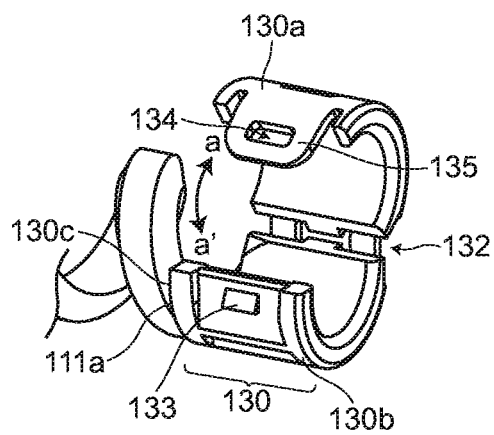
FIG.3A   FIG.3B
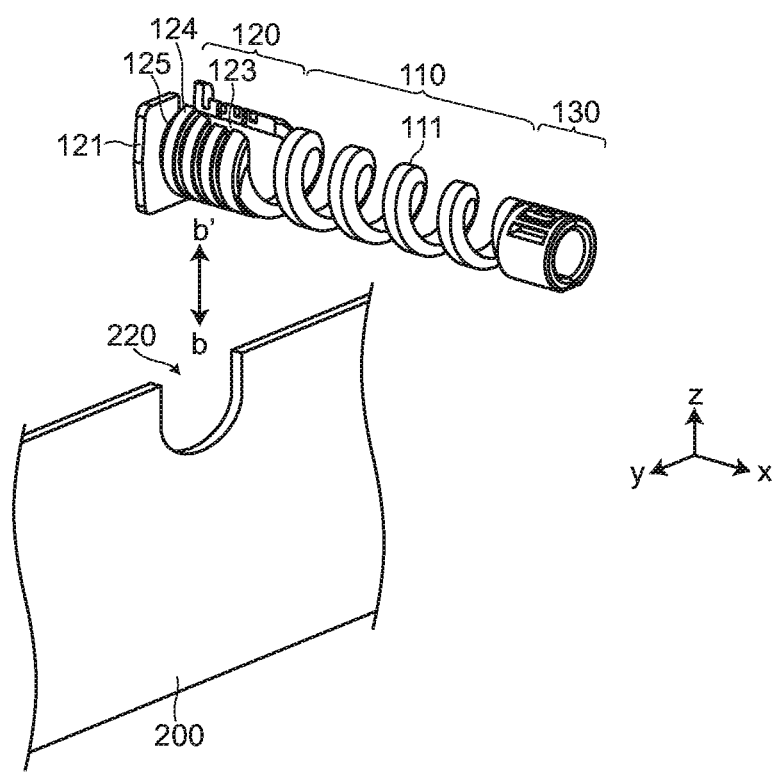
FIG.4

AUXILIARY ARTIFICIAL HEART SYSTEM

RELATED APPLICATIONS

The present application claims priority to Japanese Patent Application No. 2016-226300 filed Nov. 21, 2016, the disclosures of which is hereby incorporated by reference herein in its entirety.

BACKGROUND OF THE INVENTION

1. Field of the Invention

The present invention relates to a cable protector for preventing a cable connected to an equipment operating part accommodated in the inside of an equipment housing from being bent at a cable exit portion of the equipment housing, the cable protector being mounted on the cable exit portion of the equipment housing.

2. Description of the Related Art

When a cable connected to an equipment operating part accommodated in the inside of a housing of an electric equipment (referred to as equipment housing) is repeatedly bent at a cable exit portion of the equipment housing, there is a possibility that the cable breaks.

To prevent a cable connected to an equipment operating part accommodated in the inside of an equipment housing from being bent at a cable exit portion of the equipment housing, in many cases, a cable protector is mounted on the cable exit portion of the equipment housing. Various proposals have been made with respect to such a cable protector (see JP-A-2016-86600 (patent document 1), for example).

FIG. 8 is a view for explaining a cable protector described in patent document 1. As shown in FIG. 8, a cable protector 800 described in patent document 1 includes: a cylindrical protective tube 810 wound helically; and a mounting adapter 820 provided for mounting the protective tube 810 on an equipment housing (not shown in the drawing). The mounting adapter 820 includes a flange portion 821 and a cylindrical portion 822. The protective tube 810 and the mounting adapter 820 are provided as parts separate from each other. The protective tube 810 and the mounting adapter 820 are connected to each other by making female threads 811 formed on an inner peripheral surface side of the protective tube 810 and male threads 823 formed on an outer peripheral surface of the cylindrical portion 822 of the mounting adapter 820 engage with each other.

The cable protector 800 having such a configuration is configured to be arranged such that a center axis Ox of the cylindrical portion 822 of the mounting adaptor 820 and a center axis (not shown in the drawing) of a cable passing hole (not shown in the drawing) of the equipment housing are made to agree with each other thus fixing the flange portion 821 to the equipment housing by a screw (not shown in the drawing) or the like. Then, a cable 900 is made to pass through the inside of the protective tube 810 along the center axis Ox, and the cable 900 is connected to an equipment operating part (not shown in the drawing) accommodated in the inside of the equipment housing.

With the use of such a cable protector 800, even when the cable 900 tends to bend at a cable exit portion of the equipment housing, a bending force is absorbed by the cable protector 800 and hence, it is possible to prevent breaking of the cable 900.

SUMMARY OF INVENTION

However, in the equipment which uses the cable protector 800 shown in FIG. 8, in the case where a bending force repeatedly acts on the cable 900, although breaking of the cable 900 may be prevented, there is also a possibility that the cable protector 800 itself breaks. Further, there is also a possibility that the cable protector 800 breaks due to deterioration with a lapse of time. When the cable protector 800 breaks, in an exchanging operation of the cable protector 800, with respect to the cable protector 800 described in patent document 1, it is necessary to remove the cable 900 from the equipment operating part and, then, to take out the cable protector 800 from the cable 900.

That is, in the cable protector 800 described in patent document 1, the cable 900 is made to pass through the cable protector 800 along the center axis Ox of the cylindrical protective tube 810 and the cylindrical portion 822 of the mounting adapter 820. Accordingly, in an exchanging operation of the cable protector 800, it is necessary to perform the operation in such a manner that the cable 900 is brought into a state where the cable 900 is removed from the equipment operating part, and the cable protector 800 is removed from the cable 900 by pulling out the cable 900 from the cable protector 800.

In the case where the cable 900 is a cable for supplying power source, a cable for controlling other equipment or the like, for example, in an exchanging operation of the cable protector 800, in all these cases, there is no way but to interrupt an operation of the equipment operating part. Incase of an equipment where the interruption of the operation of the equipment operating part does not matter, no serious problem arises. However, in case of an equipment where the interruption of the operation of the equipment operating part is not preferable, in an exchanging operation of the cable protector 800, it is desirable that the cable protector 800 can be exchanged by a simple operation within a short time without removing the cable 900 from the equipment operating part.

For example, assume a case where, for example, the cable 900 is a connection cable 560 which connects a blood pump 510 which forms a part of an auxiliary artificial heart system 500 shown in FIG. 7 and is embedded in the inside of a body and a control unit 540 which is accommodated in the portable control unit accommodating housing 550 disposed outside the body to each other. In this case, it is important that the cable protector 800 can be exchanged by a simple operation within a short time without removing the connection cable 560 from an equipment operating part (the control unit 540 in FIG. 7) accommodated in the control unit accommodating housing 550.

The configuration shown in FIG. 7 is described in detail in "Description of Embodiments" described later and hence, the configuration is described in a simplified manner in this SUMMARY OF INVENTION. The auxiliary artificial heart system 500 shown in FIG. 7 includes: a blood pump 510 embedded in the body, artificial blood vessels 520, 530 for connecting the blood pump 510 and a blood flow in the heart; the portable control unit accommodating housing 550 which houses the control unit 540 for controlling the blood pump 510 outside the body; and a connection cable 560 for an auxiliary artificial heart disposed between the blood pump 510 and the control unit 540.

In the auxiliary artificial heart system 500 shown in FIG. 7, there may be a case where the connection cable 560 incorporates therein not only an electric signal line for controlling the blood pump but also a purge liquid circulation tube (not shown in the drawing) for circulating a liquid (referred to as a purge liquid) having a function of maintaining lubrication, cooling and sealability of the inside of the blood pump. In this case, the control unit 540 accommodated in the inside of the above-mentioned portable control unit accommodating housing 550 further includes a purge liquid circulation device (not shown in the drawing) for circulating a purge liquid besides an electric control part which performs an electric control.

With respect to the auxiliary artificial heart system 500 having such a configuration, assume that the cable protector 800 described in patent document 1 (see FIG. 8) is used as a cable protector 100 mounted on a cable exit portion 551 of the control unit accommodating housing 550. In exchanging such a cable protector 800, it is necessary to remove an electric signal cable and the purge liquid circulation tube incorporated in the connection cable 560 from the control unit 540 respectively thus giving rise to various problems. That is, when the electric signal cable and the purge liquid circulation tube are removed from the control unit 540, a function of the auxiliary artificial heart system is interrupted for even a temporary moment. Further, when a purge liquid which is made to circulate in the purge liquid circulation tube is exposed to outside air, there arises a drawback that the auxiliary artificial heart system 500 cannot be maintained in a non-bacterial state.

Particularly, in the auxiliary artificial heart system, there is a possibility that the portable control unit accommodating housing 550 moves in various directions with respect to the connection cable 560 frequently and hence, the cable protector 800 (cable protector 100 in FIG. 7) is liable to be easily deteriorated or broken. In view of such circumstances, with respect to the connection cable 560 used in the auxiliary artificial heart system, in exchanging the cable protector 800 (the cable protector 100 in FIG. 7), it is important that the cable protector 800 (the cable protector 100 in FIG. 7) can be exchanged in a state where the function of the auxiliary artificial heart system is maintained. To enable an exchange of the cable protector 800 in a state where the function of the auxiliary artificial heart system is maintained, it gives rise to the task of cable protector 800 being able to be exchanged by a simple operation within a short time without removing the connection cable 560 from the equipment operating part (control unit 540).

Such a task may also exist as a similar task in other equipment besides the auxiliary artificial heart system. For example, although not shown in the drawings, also in an industrial robot device disposed in a manufacture line or the like, during a period where the industrial robot device is being operated, it is important to decrease the number of stoppages of the operation as much as possible. Also in such a robot device, in exchanging a cable protector, one of the tasks is the cable protector being able to be exchanged by a simple operation within a short time without removing the connection cable from the equipment operating part.

The present invention has been made in view of the above-mentioned circumstances, and it is an object of the present invention to provide a cable protector for preventing a cable connected to an equipment operating part accommodated in the inside of an equipment housing from being bent at a cable exit portion of the equipment housing, the cable protector being mounted on the cable exit portion of the equipment housing, wherein the cable protector is particularly characterized in that, in exchanging the cable protector, the cable protector can be exchanged by a simple operation within a short time without removing the connection cable from the equipment operating part.

[1] According to an aspect of the present invention, there is provided a cable protector for preventing a cable connected to an equipment operating part accommodated in the inside of an equipment housing from being bent at a cable exit portion of the equipment housing, the cable protector being mounted on the cable exit portion of the equipment housing, wherein assuming an equipment housing side of the cable protector as a rear end side, and a side of the cable protector opposite to the rear end side as a distal end side, the cable protector includes: a helical portion which is formed of a strip-like member wound helically, the strip-like member being configured to helically surround a barrel portion of the cable; an equipment housing mounting portion which is formed on a rear-end-side end portion of the strip-like member, and is configured to surround the barrel portion of the cable between the rear-end-side end portion of the strip-like member and the equipment housing; and a distal-end-side cylindrical portion which is formed on a distal-end-side end portion of the strip-like member, and is configured to surround the barrel portion of the cable on a more distal end side than the distal-end-side end portion of the strip-like member, and the equipment housing mounting portion includes: an equipment housing mounting plate which is detachably mountable on the equipment housing; and a cylindrical body which is mounted on the equipment housing mounting plate in a projecting manner from the equipment housing mounting plate toward the distal end side, a distal-end-side end portion of the cylindrical body is connected to the rear-end-side end portion of the strip-like member, and the equipment housing mounting portion forms a notched portion thereon for allowing entering and exiting of the barrel portion of the cable into and from the equipment housing mounting portion within a range from the distal-end-side end portion of the cylindrical body to the rear-end-side end portion of the equipment housing mounting plate, the distal-end-side cylindrical portion has an opening/closing portion capable of changing over a state between a surrounding state where the distal-end-side cylindrical portion surrounds the barrel portion of the cable over the whole circumference along a circumferential direction and a state which allows entering and exiting of the barrel portion of the cable into and from the distal-end-side cylindrical portion.

According to the cable protector of the present invention, with such a configuration, in exchanging the cable protector, the cable protector can be exchanged by a simple operation within a short time without removing the connection cable from the equipment operating part.

[2] In the cable protector according to the present invention, it is preferable that the opening/closing portion which the distal-end-side cylindrical portion has be configured to be openable and closable in a predetermined region along a circumferential direction out of a whole peripheral surface of the distal-end-side cylindrical portion.

Since the distal-end-side cylindrical portion has such a configuration, the cable can be taken out in a state where the opening/closing portion is opened, and the cable can be brought into a state where the cable is held over the whole circumferential direction in a state where the opening/closing portion is closed. Accordingly, by bringing the opening/closing portion in a closed state in a state where the cable protector is mounted on the cable, the cable is brought into a state where the cable is held over the whole circumferential direction and hence, it is possible to prevent the cable from being removed along the strip-like member wound helically.

[3] In the cable protector according to the present invention, it is preferable that the helical portion, the equipment housing mounting portion and the distal-end-side cylindrical portion be integrally formed with each other.

With such a configuration, the cable protector according to the present invention can be manufactured as one part and hence, the reduction of a manufacturing cost can be realized. Further, after the cable protector is manufactured, the cable protector is handled as one part and hence, a part management is also facilitated.

[4] In the cable protector according to the present invention, it is preferable that the equipment housing be a housing of an electric equipment, and the cable be an electric cable.

As a housing of an electric equipment, for example, an equipment housing in which a control unit for controlling an industrial robot device is accommodated can be exemplified. In an industrial robot device disposed in a manufacture line or the like, during a period where the industrial robot device is being operated, it is important to decrease the number of stoppages of the operation as much as possible. With the cable protector according to the present invention, even in such an industrial robot device, in exchanging the cable protector, the cable protector can be exchanged without removing the cable from the control unit which forms an equipment operating part. Accordingly, also in exchanging the cable protector, it is unnecessary to stop an operation of the industrial robot device.

[5] In the cable protector according to the present invention, it is preferable that the equipment housing be a control unit accommodating housing for accommodating a control unit for controlling a blood pump for an auxiliary artificial heart embedded in a body outside the body, the cable be a connection cable for the auxiliary artificial heart which connects the blood pump and the control unit to each other, and an electric signal line be incorporated in the connection cable.

With the use of the cable protector according to the present invention in such an auxiliary artificial heart system, in exchanging the cable protector, the cable protector can be exchanged without removing the connection cable. In this manner, with the use of the cable protector according to the present invention in the auxiliary artificial heart system, there is no possibility that a function of the auxiliary artificial heart system is interrupted due to an exchange of the cable protector and hence, the cable protector can be exchanged in a state where the function of the auxiliary artificial heart system is maintained.

[6] In the cable protector according to the present invention, it is preferable that a purge liquid circulation device for circulating a purge liquid having a function of maintaining lubrication, cooling and sealability of the blood pump be further accommodated in the control unit, and a purge liquid circulating pipe for circulating the purge liquid be further incorporated in the connection cable for the auxiliary artificial heart.

With the use of the cable protector according to the present invention in such an auxiliary artificial heart system, also in exchanging the cable protector, there is no possibility that the connection cable is removed and hence, it is unnecessary to remove the purge liquid circulation tube incorporated in the connection cable from the control unit. Accordingly, it is possible to obviate the occurrence of "a drawback that a purge liquid which circulates in the purge liquid circulation tube is exposed to outside air thus giving rise to a case where a non-bacterial state cannot be maintained".

BRIEF DESCRIPTION OF DRAWINGS

FIG. 3A and FIG. 3B are views showing a distal-end-side cylindrical portion 130 of the cable protector 100 in an enlarged manner.

FIG. 4 is a view for explaining steps of mounting the cable protector 100 according to the embodiment on the equipment housing 200;

DESCRIPTION OF EMBODIMENTS

Hereinafter, an embodiment of the present invention is described.

Figure 1:
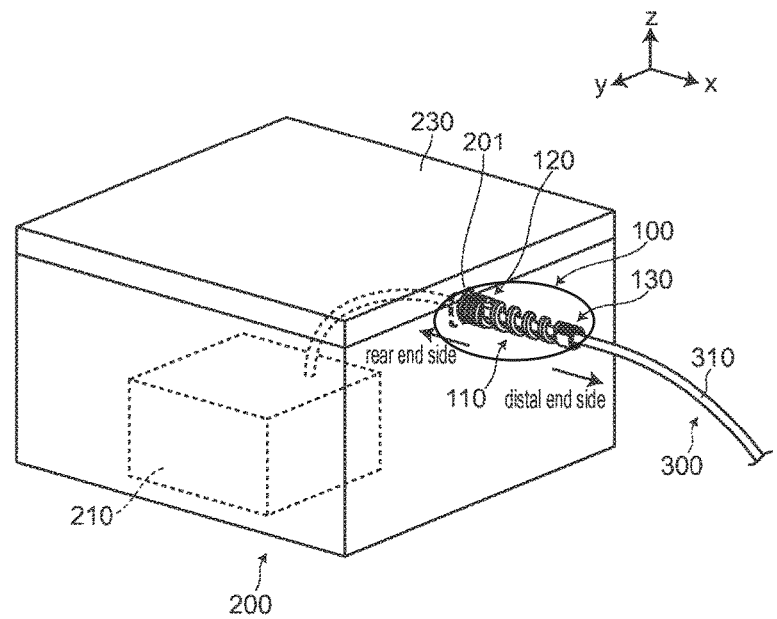
FIG. 1 is a view showing a state where a cable protector 100 according to an embodiment is mounted on an equipment housing.

FIG. 1 is a view showing a state where a cable protector 100 according to the embodiment is mounted on an equipment housing 200.

Figure 2:
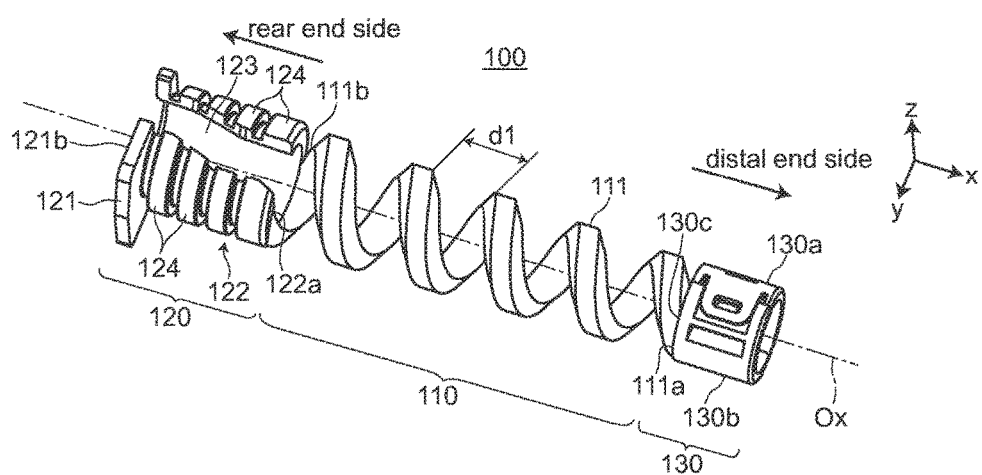
FIG. 2 is a view for explaining the cable protector 100 according to the embodiment.

FIG. 2 is a view for explaining the cable protector 100 according to the embodiment. FIG. 2 is a view showing, in an enlarged manner, the cable protector 100 according to the embodiment in a state where the cable protector 100 is removed from the equipment housing 200 shown in FIG. 1.

First, the cable protector 100 according to the embodiment is described with reference to FIG. 1 and FIG. 2. In the description made hereinafter, there may be a case where "the cable protector 100 according to the embodiment" is simply referred to as "cable protector 100".

As shown in FIG. 1, an equipment operating part 210 is accommodated in the inside of the equipment housing 200 of an electric equipment or the like, and a cable 300 is connected to the equipment operating part 210. In FIG. 1, a kind of the cable 300 is not particularly limited. An electric cable such as a cable for supplying commercial power or a cable for controlling other equipment can be exemplified as the cable 300. The cable 300 passes through the inside of the cable protector 100 mounted on a cable exit portion 201 of the equipment housing 200 and extends to the outside of the equipment housing 200. In the description made hereinafter, an equipment housing 200 side of the cable protector 100 is assumed as a rear end side, and a side of the cable protector 100 opposite to the rear end side of the cable protector 100 is assumed as a distal end side.

As shown in FIG. 2, the cable protector 100 includes: a helical portion 110 which is formed of a strip-like member 111 wound in a helical manner and helically surrounds a barrel portion 310 of the cable 300 by the strip-like member 111; an equipment housing mounting portion 120 which is formed on a rear-end-side end portion 111b of the strip-like member 111 and surrounds the barrel portion 310 of the cable 300 between a rear-end-side end portion 111b of the strip-like member 111 and the equipment housing 200; and a distal-end-side cylindrical portion 130 which is formed on a distal-end-side end portion 111a of the strip-like member 111 and surrounds the barrel portion 310 of the cable 300 within a predetermined range more on a distal end side than the distal-end-side end portion 111a of the strip-like member 111.

The cable protector 100 according to the embodiment is further described.

The strip-like member 111 of the helical portion 110 is wound at a pitch dl along an x axis (center axis Ox). Here, the pitch dl is a pitch large enough for taking out the barrel portion 310 of the cable 300.

The equipment housing mounting portion 120 includes: an equipment housing mounting plate 121 which is detachably mountable on the equipment housing 200 (hereinafter, the equipment housing mounting plate 121 also being simply referred to as "mounting plate 121"); and a cylindrical body 122 which is formed on the mounting plate 121 in a projecting manner from the mounting plate 121 toward a distal end side (a helical portion 110 side). The cylindrical body 122 has a distal-end-side end portion 122a which is connected to the rear-end-side end portion 111b of the strip-like member 111.

A notched portion 123 which allows entering and exiting of the barrel portion 310 of the cable 300 into and from the equipment housing mounting portion 120 is formed on the equipment housing mounting portion 120 within a range from the distal-end-side end portion 122a of the cylindrical body 122 to a rear-end-side end portion 121b of the mounting plate 121. The notched portion 123 has a width large enough for taking out the barrel portion 310 of the cable 300 from the equipment housing mounting portion 120.

A plurality of ribs 124 are formed on an outer peripheral surface of the cylindrical body 122 of the equipment housing mounting portion 120 at predetermined intervals. With such a configuration, in external appearance, the cylindrical body 122 is formed into a shape where a recessed portion and a projecting portion are alternately formed.

The distal-end-side cylindrical portion 130 has an opening/closing portion 130a capable of switching a state of the distal-end-side cylindrical portion 130 between a surrounding state where the distal-end-side cylindrical portion 130 surrounds the barrel portion 310 of the cable 300 and a state which allows entering and exiting of the barrel portion 310 of the cable 300 into and from the distal-end-side cylindrical portion 130. Further, the distal-end-side cylindrical portion 130 has a rear-end-side end portion 130c which is connected to the distal-end-side end portion 111a of the strip-like member 111.

FIG. 3A and FIG. 3B are views showing the distal-end-side cylindrical portion 130 in an enlarged manner. FIG. 3A shows a state where the opening/closing portion 130a is closed, and FIG. 3B shows a state where the opening/closing portion 130a is opened. The distal-end-side cylindrical portion 130 is further described hereinafter.

A hinge portion 132 is formed on the distal-end-side cylindrical portion 130 between a distal-end-side end portion and the rear-end-side end portion of the distal-end-side cylindrical portion 130 along the center axis Ox (see FIG. 2). With such a configuration, as shown in FIG. 3B, out of the whole peripheral surface of the distal-end-side cylindrical portion 130, the opening/closing portion 130a is configured such that a predetermined region of the opening/closing portion 130a disposed along a circumferential direction can be opened or closed in a direction indicated by an arrow a-a' using the hinge portion 132 as a fulcrum. In this specification, assume that "a predetermined region of the opening/closing portion 130a disposed along a circumferential direction out of the whole peripheral surface of the distal-end-side cylindrical portion 130" is a region which corresponds to approximately one half of the whole circumference along the circumferential direction of the distal-end-side cylindrical portion 130. A portion of the distal-end-side cylindrical portion 130 other than the opening/closing portion 130a is assumed as "fixed portion 130b".

With such a configuration, a state of the distal-end-side cylindrical portion 130 can be switched between a surrounding state where the distal-end-side cylindrical portion 130 surrounds the barrel portion 310 of the cable 300 and a state which allows entering and exiting of the barrel portion 310 of the cable 300 into and from the distal-end-side cylindrical portion 130.

In the distal-end-side cylindrical portion 130 having such a configuration, a hook portion 133 and an engaging portion (for example, a hole portion) 134 with which the hook portion 133 is engaged are formed on a contact portion between the opening/closing portion 130a and the fixed portion 130b. In the cable protector 100 according to the embodiment, the hook portion 133 is formed on a fixed portion 130b side, and the hole portion 134 is formed on an opening/closing portion 130a side. The hole portion 134 is formed on a pawl plate portion 135 formed on the opening/closing portion 130a.

Since the distal-end-side cylindrical portion 130 has such a configuration, when the opening/closing portion 130a is brought into a state where the opening/closing portion 130a is closed with respect to the fixed portion 130b (see FIG. 3A), the hook portion 133 formed on the fixed portion 130b is engaged with the hole portion 134 formed on the pawl plate portion 135 of the opening/closing portion 130a, and both the opening/closing portion 130a and the fixed portion 130b are maintained in a closed state unless a user intentionally performs an opening operation. With such a configuration, in a state where the cable protector 100 is mounted on the cable 300, by bringing the opening/closing portion 130a into a closed state, the cable 300 is held over the whole circumferential direction and hence, it is possible to prevent the occurrence of a phenomenon where the cable 300 is removed along the strip-like member 111 which is helically wound around the cable 300.

When a user wants to open the opening/closing portion 130a from a state where the opening/closing portion 130a is closed, he engages his nail with the pawl plate portion 135 and pulls up the opening/closing portion 130a so that the hole portion 134 is removed from the hook portion 133 whereby the user can bring the opening/closing portion 130a into an open state (see FIG. 3B).

The cable protector 100 having the above-mentioned configuration is made of a synthetic resin, elastomer or the like, for example. In the cable protector 100 according to this embodiment, the helical portion 110, the equipment housing mounting portion 120 and the distal-end-side cylindrical portion 130 are integrally formed with each other. Accordingly, the cable protector 100 is configured such that the parts of the cable protector 100 ranging from the equipment housing mounting portion 120 to the distal-end-side cylindrical portion 130 are continuously and integrally connected to each other.

As described above, the cable protector 100 is configured such that the helical portion 110, the equipment housing mounting portion 120 and the distal-end-side cylindrical portion 130 are integrally formed with each other and hence, the cable protector 100 can be manufactured as one part. Accordingly, the reduction of manufacturing cost can be realized. Further, after the cable protector 100 is manufactured, the cable protector 100 can be handled as one part and hence, control of parts can be facilitated.

FIG. 4 is a view for explaining steps of mounting the cable protector 100 according to the embodiment on the equipment housing 200. In FIG. 4, only a portion of the equipment housing 200 is shown, and the illustration of the cable 300 is omitted. In FIG. 4, the indication of symbols which correspond to portions which do not need to be specifically described are omitted.

As shown in FIG. 4, a U-shaped notched portion 220 for mounting the cable protector 100 according to the embodiment on the equipment housing 200 is formed on the equipment housing 200. By inserting the cable protector 100 into the U-shaped notched portion 220 along a z axis in a direction indicated by an arrow b, the cable protector 100 can be mounted on the equipment housing 200.

That is, by inserting the cable protector 100 in the direction indicated by an arrow b along the z axis such that the mounting plate 121 is brought into contact with an inner surface of the equipment housing 200, a recessed portion 125 between the mounting plate 121 and the rib 124 is engaged with the U-shaped notched portion 220 thus enabling mounting of the cable protector 100 on the equipment housing 200. In such an operation, for example, as shown in FIG. 1, by mounting an upper lid 230 on an upper surface side of the equipment housing 200 thus restricting the upward movement of the mounting plate 121, there is no possibility that the cable protector 100 is removed from the equipment housing 200. On the other hand, in removing the cable protector 100 from the equipment housing 200, by removing the upper lid 230 and by pulling out the cable protector 100 in a direction indicated by an arrow b' along the Z axis, the cable protector 100 can be easily removed from the equipment housing 200.

The cable protector 100 is mounted on the equipment housing 200 as described above, and the cable 300 which is connected to the equipment operating part 210 (see FIG. 1) accommodated in the inside of the equipment housing 200 is made to pass through the inside of the cable protector 100 along the center axis Ox and, thereafter, the cable 300 is extended to the outside. With such a configuration, even when the cable 300 tends to bend at the cable exit portion 201 of the equipment housing 200, a bending force of the cable 300 is absorbed by the cable protector 100 and hence, it is possible to prevent breaking of the cable 300.

When a bending operation of the cable 300 is repeatedly performed, there may be a case where the cable protector 100 breaks. There may be also a case where the cable protector 100 breaks due to deterioration with a lapse of time. In this case, it is necessary to exchange the cable protector 100. Next, steps of exchanging the cable protector 100 mounted on the cable 300 as shown in FIG. 1 are described.

FIG. 5A to FIG. 5D are views for explaining steps of removing the cable protector 100 from the cable 300 in exchanging the cable protector 100. In FIG. 5A to FIG. 5D, the cable protector 100 and the cable 300 are shown in an enlarged manner, while the illustrations of the equipment housing 200, the equipment operating part 210 and the like are omitted. In FIG. 5A to FIG. 5D, the indication of symbols which correspond to portions which do not need to be specifically described are omitted.

Figure 5A:
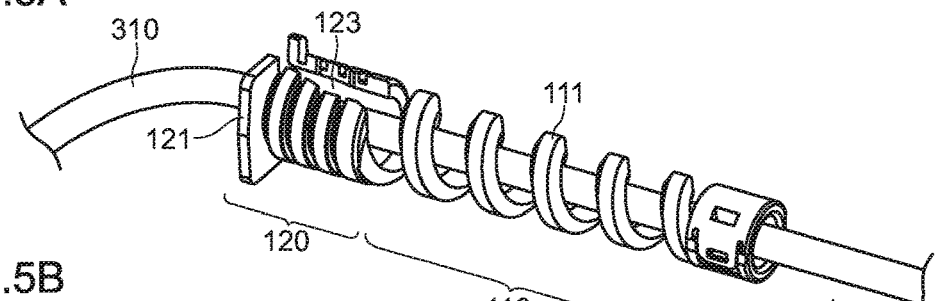
FIG. 5A to FIG. 5D are views for explaining steps of removing the cable protector 100 from a cable 300 at the time of exchanging the cable protector 100.
Figure 5B:
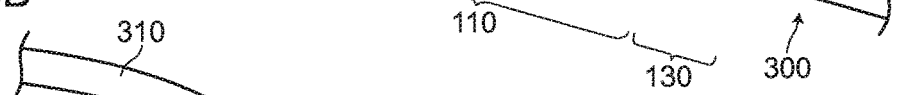

First, the upper lid 230 of the equipment housing 200 is removed (see FIG. 1), and the cable protector 100 is removed from the equipment housing 200 in a state where the cable 300 is made to pass through the cable protector 100 (see FIG. 5A). At this stage of the operation, a connection state of the cable 300 to the equipment operating part 210 (see FIG. 1) accommodated in the inside of the equipment housing 200 may be maintained as it is.

Figure 5C:
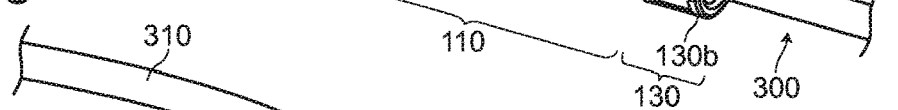
Figure 5D:
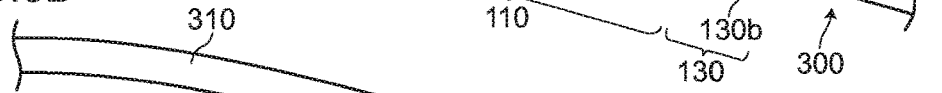
Figure 5D:
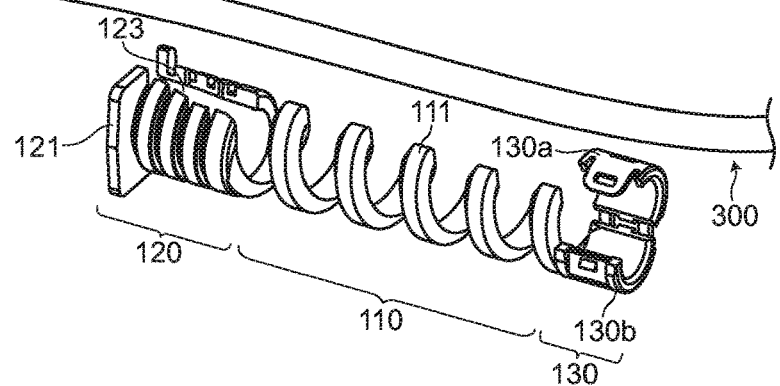

In a state shown in FIG. 5A, the barrel portion 310 of the cable 300 is taken out from the notched portion 123 of the equipment housing mounting portion 120 of the cable protector 100 (see FIG. 5B), and the barrel portion 310 of the cable 300 is removed from the helical portion 110 along the strip-like member 111 which is wound helically (see FIG. 5C). FIG. 5C shows a state where the barrel portion 310 of the cable 300 is removed from the helical portion 110 up to a portion of the cable 300 which corresponds to approximately one half of the helical portion 110. At this point of time, assume that the opening/closing portion 130a of the distal-end-side cylindrical portion 130 of the cable protector 100 is in an open state (see FIG. 3B).

By further continuing such an operation, the cable 300 can be removed from the helical portion 110 up to a portion of the cable 300 just in front of the distal-end-side cylindrical portion 130. Then, by taking out the barrel portion 310 of the cable 300 from the opening/closing portion 130a of the distal-end-side cylindrical portion 130, the cable protector 100 can be removed from the cable 300 (see FIG. 5D). With respect to a timing at which the opening/closing portion 130a of the distal-end-side cylindrical portion 130 is opened, the opening/closing portion 130a may be opened in advance at a point of time when the removal of the cable 300 is started (in a state shown in FIG. 5A) or may be opened at a point of time when the cable 300 is removed up to a portion of the cable 300 just in front of the distal-end-side cylindrical portion 130.

As described above, according to the cable protector 100 of the embodiment, in removing the cable protector 100, the cable protector 100 can be removed while maintaining a state where the cable 300 is connected to the equipment operating part 210 disposed in the inside of the equipment housing 200.

In exchanging the cable protector 100, in FIG. 5A to FIG. 5D, the cable 300 is taken out in a direction from an equipment housing mounting portion 120 side toward a distal-end-side cylindrical portion 130 side. However, the cable 300 may be taken out in a direction from the distal-end-side cylindrical portion 130 side toward the equipment housing mounting portion 120 side.

As has been described above, when the removal of the damaged cable protector 100 is finished, a new cable protector 100 is mounted. Hereinafter, steps of mounting the new cable protector 100 are described. The steps of mounting the new cable protector 100 can be performed in order of steps substantially opposite to the order of steps of removing the cable protector 100 and hence, the steps of mounting the new cable protector 100 are described in a simplified manner. Also in this case, a connection state of the cable 300 to the equipment operating part 210 existing in the inside of the equipment housing 200 may be maintained as it is.

Figure 6A:
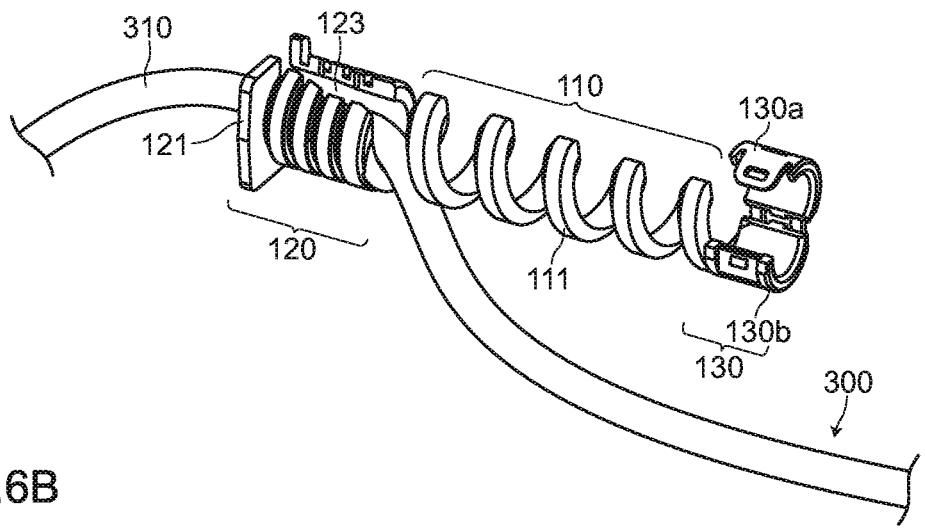
FIG. 6A to FIG. 6C are views for explaining steps of mounting the cable protector 100 on the cable 300 at the time of exchanging the cable protector 100.
Figure 6B:
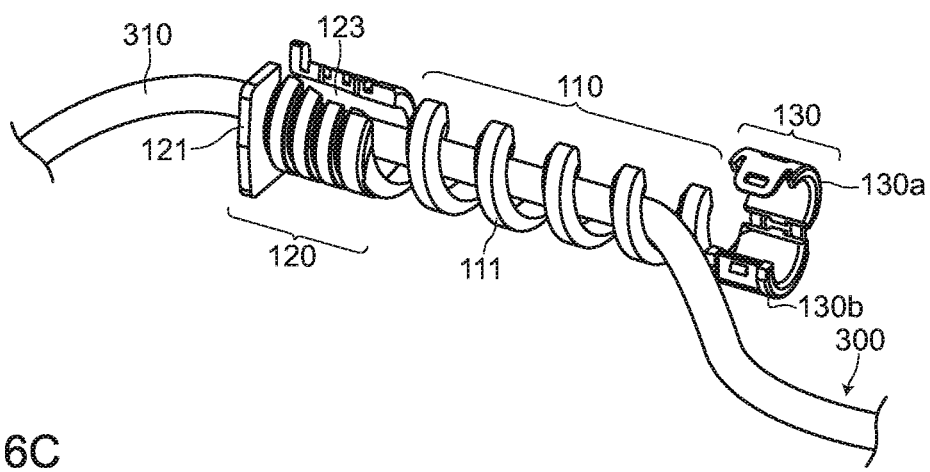
Figure 6C:
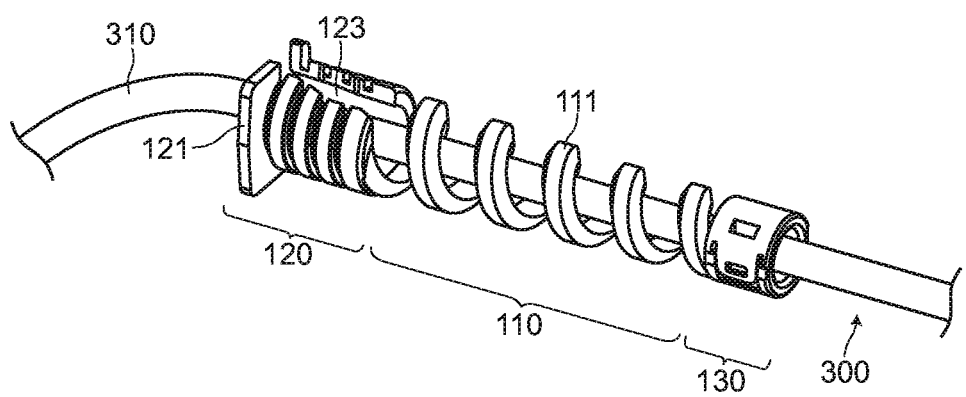

FIG. 6A to FIG. 6C are views for explaining steps of mounting the cable protector 100 on the cable in exchanging the cable protector 100. In FIG. 6A to FIG. 6C, the cable protector 100 and the cable 300 are shown in an enlarged manner, and the illustrations of the equipment housing 200, the equipment operating part 210 and the like are omitted. In FIG. 6A to FIG. 6C, the indication of symbols which correspond to portions which do not need to be specifically described are omitted.

First, the opening/closing portion 130a of the distal-end-side cylindrical portion 130 is brought into an open state.

Then, the barrel portion 310 of the cable 300 is inserted into the cable protector 100 along the notched portion 123 of the equipment housing mounting portion 120 of the cable protector 100, and the barrel portion 310 of the cable 300 is inserted into the cable protector 100 along the strip-like member 111 which is wound helically (see FIG. 6A).

By further continuing such an operation, the barrel portion 310 of the cable 300 can be inserted up to a portion of the barrel portion 310 just in front of the distal-end-side cylindrical portion 130 (see FIG. 6B). Then, the barrel portion 310 of the cable 300 is inserted into the distal-end-side cylindrical portion 130 and the opening/closing portion 130a is closed (see FIG. 6C). By closing the opening/closing portion 130a of the distal-end-side cylindrical portion 130, in a state where the cable protector 100 is mounted on the cable 300, it is possible to prevent the occurrence of a phenomenon where the barrel portion 310 of the cable 300 is removed along the strip-like member 111 which is wound helically thus maintaining a state shown in FIG. 6C. Thereafter, an assembly where the cable protector 100 is mounted on the cable 300 (see FIG. 6C) is mounted on the equipment housing 200 as shown in FIG. 1.

As described above, according to the cable protector 100 of the embodiment, also in mounting the new cable protector 100 on the equipment housing 200, the new cable protector 100 can be mounted while maintaining a state where the cable 300 is connected to the equipment operating part 210 disposed in the inside of the equipment housing 200.

In FIG. 6A to FIG. 6C, the cable 300 is inserted into the cable protector 100 in a direction from an equipment housing mounting portion 120 side toward a distal-end-side cylindrical portion 130 side. However, the cable 300 may be inserted into the cable protector 100 in a direction from the distal-end-side cylindrical portion 130 side toward the equipment housing mounting portion 120 side.

Figure 7:
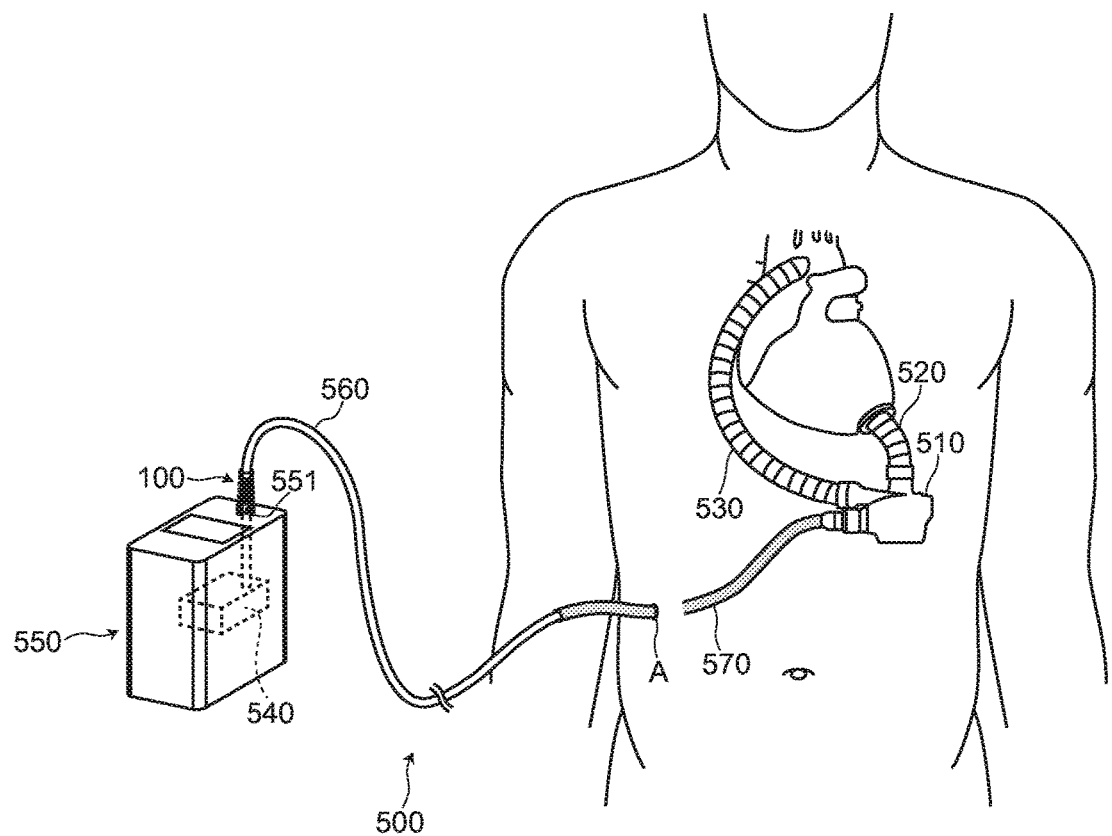
FIG. 7 is a view for explaining a case where the cable protector 100 according to the embodiment is used in an auxiliary artificial heart system 500.
Figure 8:
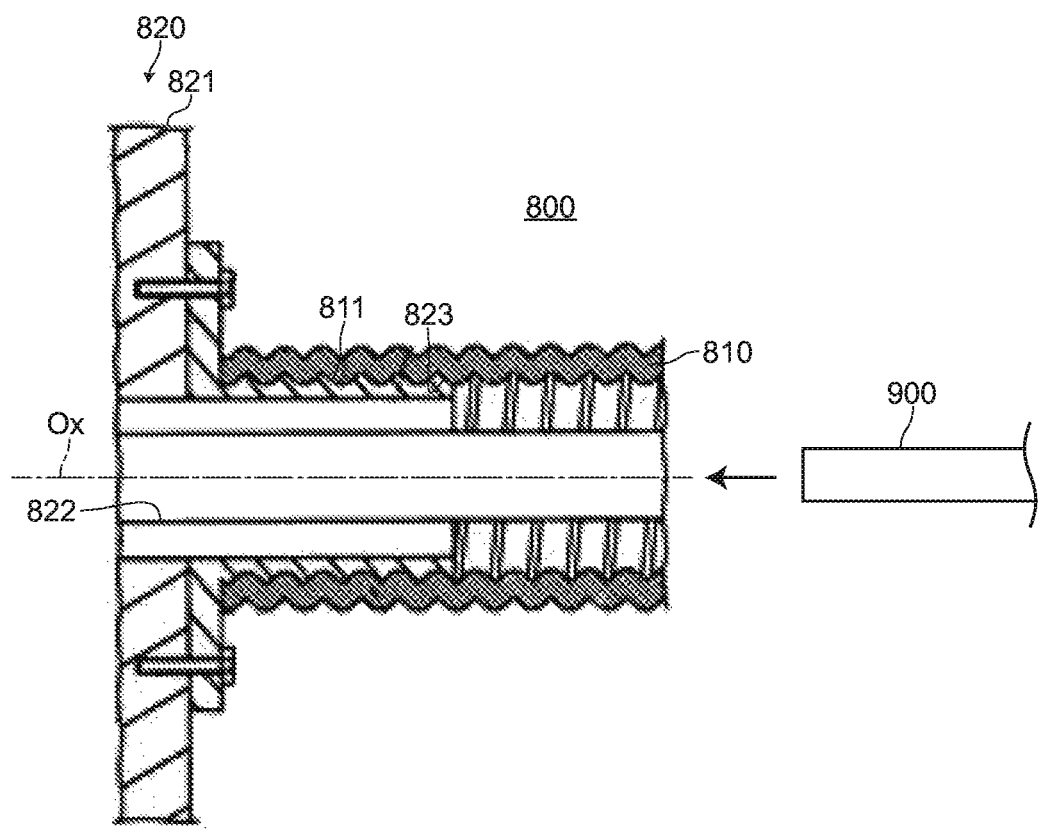
FIG. 8 is a view for explaining a cable protector 800 described in the patent literature 1.

FIG. 7 is a view for explaining a case where the cable protector 100 according to the embodiment is used in an auxiliary artificial heart system 500. As shown in FIG. 7, the auxiliary artificial heart system 500 includes: a blood pump 510 embedded in a body, artificial blood vessels 520, 530 for connecting the blood pump 510 to a blood flow in a heart; a portable control unit accommodating housing 550 which houses a control unit 540 for controlling the blood pump 510 outside the body; and a connection cable 560 for an auxiliary artificial heart disposed between the blood pump 510 and the control unit 540. The cable protector 100 according to the embodiment is mounted on a cable exit portion 551 through which the connection cable 560 extends to the outside of the control unit accommodating housing 550.

With respect to the auxiliary artificial heart system 500 shown in FIG. 7, a purge liquid having a function of maintaining lubrication, cooling and sealability of the inside of the blood pump 510 is made to circulate in the auxiliary artificial heart system 500. Further, a transubstantiated artificial fabric (also referred to as a fabric) 570 is mounted on the connection cable 560 at least between an entrance portion A to the body and the blood pump 510 between the blood pump 510 and the control unit 540 in such a manner that the transubstantiated artificial fabric 570 covers a surface of the connection cable 560.

In an example shown in FIG. 7, the cable exit portion 551 of the control unit 540 is formed on an upper end surface of the control unit accommodating housing 550 and hence, it is assumed that the cable protector 100 is mounted on the upper end surface of the control unit accommodating housing 550.

The control unit accommodating housing 550 shown in FIG. 7 corresponds to the equipment housing 200 in FIG. 1, the control unit 540 accommodated in the control unit accommodating housing 550 shown in FIG. 7 corresponds to the equipment operating part 210 shown in FIG. 1, and the connection cable 560 shown in FIG. 7 corresponds to the cable 300 shown in FIG. 1. However, as described above, the auxiliary artificial heart system 500 shown in FIG. 7 is configured to circulate a purge liquid having a function of maintaining lubrication, cooling and sealability of the inside of the blood pump 510 and hence, a purge liquid circulation device (not shown in the drawing) for circulating the purge liquid is also accommodated in the inside of the control unit 540. The connection cable 560 incorporates therein not only an electric signal line (not shown in the drawing) for controlling the blood pump 510 but also a purge liquid circulation tube (not shown in the drawing) for circulating a purge liquid.

In the auxiliary artificial heart system 500 shown in FIG. 7, as described above, it is important that the cable protector can be exchanged without removing the connection cable 560 from an equipment operating part (the control unit 540). This is because, as described previously, when an electric signal cable and a purge liquid circulation tube incorporated in the connection cable 560 are removed from the control unit 540, a function of the auxiliary artificial heart system 500 is interrupted for even a temporary moment. Further, when a purge liquid which is made to circulate in the purge liquid circulation tube is exposed to outside air, there arises a drawback that the auxiliary artificial heart system 500 may not be maintained in a non-bacterial state.

With the use of the cable protector 100 according to the embodiment in such an auxiliary artificial heart system 500, also in exchanging the cable protector 100, the cable protector 100 can be exchanged without removing the connection cable 560 from the control unit 540 by a simple operation within a short time. In this manner, with the use of the cable protector 100 according to the embodiment in the auxiliary artificial heart system 500, a possibility can be eliminated of the occurrence of the previously-described problem, that is, "a problem that when an electric signal cable and a purge liquid circulation tube incorporated in the connection cable 560 are removed from the control unit 540, a function of the auxiliary artificial heart system 500 is interrupted for even a temporary moment and, further, when a purge liquid which is made to circulate in the purge liquid circulation tube is exposed to outside air, there arises a drawback that the auxiliary artificial heart system 500 may not be maintained in a non-bacterial state".

The present invention is not limited to the above-mentioned embodiment, and various modifications are conceivable without departing from the gist of the present invention. For example, the following modifications are also conceivable.

(1) In the above-mentioned embodiment, the case is exemplified where, in mounting the cable protector 100 on the equipment housing 200, the cable protector 100 is mounted on the equipment housing 200 such that the mounting plate 121 of the equipment housing mounting portion 120 is inserted into the U-shaped notched portion 220 of the equipment housing 200. However, the present invention is not limited to such a configuration. Provided that the equipment housing mounting portion 120 can be made detachable, the mounting of the cable protector 100 can be performed by other methods. For example, the cable protector 100 may be mounted on the equipment housing 200 by threaded engagement by forming a threaded hole in the mounting plate 121 and the equipment housing 200 respectively.

(2) In the above-mentioned embodiment, the description has been made by taking the case where the cable protector 100 is manufactured such that the helical portion 110, the equipment housing mounting portion 120, and the distal-end-side cylindrical portion 130 are integrally formed with each other as an example. However, the cable protector 100 may be manufactured such that the helical portion 110, the equipment housing mounting portion 120, and the distal-end-side cylindrical portion 130 are manufactured separately from each other and, thereafter, the helical portion 110, the equipment housing mounting portion 120, and the distal-end-side cylindrical portion 130 are connected to each other.

For example, the cable protector 100 may be configured such that the helical portion 110 and the equipment housing mounting portion 120 are integrally formed with each other, the distal-end-side cylindrical portion 130 is formed as a part separate from the helical portion 110 and the equipment housing mounting portion 120, and the distal-end-side cylindrical portion 130 is detachably mountable on the distal-end-side end portion of the strip-like member 111 of the helical portion 110. In this case, the distal-end-side cylindrical portion 130 may be made of a material different from a material for forming the helical portion 110 and the equipment housing mounting portion 120.

Further, the cable protector 100 may be configured such that the helical portion 110 and the distal-end-side cylindrical portion 130 are integrally formed with each other, the equipment housing mounting portion 120 is provided as apart separate from the helical portion 110 and the distal-end-side cylindrical portion 130, and the equipment housing mounting portion 120 is detachably mountable on the rear-end-side end portion of the strip-like member 111 of the helical portion 110. In this case, the equipment housing mounting portion 120 may be made of a material different from a material for forming the helical portion 110 and the distal-end-side cylindrical portion 130.

(3) In the above-mentioned embodiment, the description has been made by taking the case where the cable protector 100 according to the embodiment is used in the auxiliary artificial heart system 500 as one example. However, the application of the cable protector 100 according to the embodiment is not limited to the auxiliary artificial heart system 500, and the cable protector 100 can be used also in an equipment whose stoppage of operation is not desired to the greatest extent possible (for example, an industrial robot device used in a manufacture line or the like).

(4) In the above-mentioned embodiment, although the description has been made mainly with respect to the case where the equipment housing is an electric equipment housing, the cable protector 100 according to the embodiment can be mounted on a cable (tube) for supplying or circulating a lubricant or the like in an equipment housing which supplies or circulates a lubricant.

What is claimed is:

1. A cable protector for an auxiliary artificial heart and a control system comprising: a cable connecting a blood pump and a control unit, the blood pump is mounted on a cable exit portion of the control unit, wherein
the cable extends from the cable exit portion toward the blood pump,
the control unit has a first notched portion where the cable protector is mounted, and the cable protector further comprises:
a control unit mounting portion, having a cylindrical body, where the cable protector is mounted;
a helical portion which helically surrounds the cable;
a cylindrical portion directed from the cable exit portion toward the blood pump;
a plurality of ribs formed on an outer peripheral surface of the cylindrical body;
a second notched portion where the cable is removably inserted;
a first end portion which is connected to the helical portion, the helical portion comprising a second end portion connected to the control unit mounting portion; and
a third end portion connected to the cylindrical portion, the cylindrical portion having a fixed portion fixing the cable, a hook portion and an engaging portion are used to facilitate an opening/closing portion where the cable is entered and exits; and
a fourth end portion connected to the helical portion.

2. The cable protector for an auxiliary artificial heart and a control system according to claim 1, wherein the helical portion, the cylindrical portion and the control unit mounting portion are integrally formed with each other, and the cable protector, ranging from the control unit mounting portion to the cylindrical portion, are continuously and integrally connected to each other.

3. The cable protector for an auxiliary artificial heart and a control system according to claim 1, wherein the control unit is a housing unit of an electric equipment, and the cable is an electric cable.

4. The cable protector for an auxiliary artificial heart and a control system according to claim 1, wherein the control unit mounting portion, the helical portion, and the cylindrical portion are integrally formed.

5. The cable protector for an auxiliary artificial heart and a control system according to claim 1, wherein a purge liquid circulation tube is incorporated in the cable.

* * * * *